(12) United States Patent
Yuan et al.

(10) Patent No.: US 9,535,054 B2
(45) Date of Patent: Jan. 3, 2017

(54) BODY FLUID TESTING APPARATUS

(71) Applicant: W.H.P.M Bioresearch & Technology Co. Ltd., Beijing (CN)

(72) Inventors: Chunhua Yuan, Beijing (CN); Qinghai Xia, Beijing (CN); John Wan, Beijing (CN)

(73) Assignee: W.H.P.M. BIORESEARCH & TECHNOLOGY CO. LTD., Beijing (CN)

( * ) Notice: Subject to any disclaimer, the term of this patent is extended or adjusted under 35 U.S.C. 154(b) by 669 days.

(21) Appl. No.: 13/933,699

(22) Filed: Jul. 2, 2013

(65) Prior Publication Data

US 2014/0007659 A1    Jan. 9, 2014

(30) Foreign Application Priority Data

Jul. 3, 2012 (CN) .......................... 2012 1 0229325

(51) Int. Cl.
    *G01N 33/493* (2006.01)
(52) U.S. Cl.
    CPC .................................. *G01N 33/493* (2013.01)
(58) Field of Classification Search
    CPC .................................................. G01N 33/493
    See application file for complete search history.

(56) References Cited

U.S. PATENT DOCUMENTS

| | | | |
|---|---|---|---|
| 4,473,530 A * | 9/1984 | Villa-Real | G01N 21/8483 215/6 |
| 4,979,402 A * | 12/1990 | Ryan | A61B 10/007 422/504 |
| 5,022,411 A * | 6/1991 | Guirguis | A61B 10/0045 600/584 |
| 5,358,690 A * | 10/1994 | Guirguis | A61B 10/0045 422/420 |
| 5,403,551 A * | 4/1995 | Galloway | A61B 10/007 422/417 |
| 5,788,863 A * | 8/1998 | Milunic | B01D 61/00 210/198.2 |
| 6,277,646 B1 * | 8/2001 | Guirguis | A61B 10/007 422/417 |
| 6,576,193 B1 | 6/2003 | Cui et al. | |

(Continued)

FOREIGN PATENT DOCUMENTS

| | | |
|---|---|---|
| CN | 201177580 Y | 1/2009 |
| WO | WO 9838917 A1 * | 9/1998 ........... A61B 10/007 |

*Primary Examiner* — John Fitzgerald
(74) *Attorney, Agent, or Firm* — Cantor Colburn LLP

(57) ABSTRACT

A body fluid testing apparatus, comprising a containing chamber having a first opening on the bottom wall thereof; a plunger chamber having a plunger contacting with the side wall thereof and having a second opening on the bottom wall thereof, wherein the plunger chamber is disposed below the bottom wall of the containing chamber and in communication with the containing chamber through the first opening; and a testing chamber having a testing card designed to contain test strips and perpendicular to the longitudinal axial of the plunger chamber, wherein the testing chamber is disposed next to the side wall of the containing chamber and in communication with the plunger chamber through the second opening. The device according to the present disclosure can carry out the test of the body fluid, even though it has no chamber on the plunger body.

17 Claims, 10 Drawing Sheets

(56) References Cited

U.S. PATENT DOCUMENTS

| | | | | |
|---|---|---|---|---|
| 7,270,959 B2* | 9/2007 | Hudak | ................... | B01L 3/502 422/537 |
| 7,300,633 B2* | 11/2007 | Hudak | ................... | B01L 3/502 422/537 |
| 7,517,495 B2* | 4/2009 | Wu | ................... | A61B 10/0045 422/550 |
| 8,394,626 B2* | 3/2013 | Ramsey | ............... | A61B 10/007 422/400 |
| 8,486,353 B2* | 7/2013 | Wu | ................... | A61B 10/007 422/557 |
| 8,511,149 B2* | 8/2013 | Lv | ................... | A61B 10/0045 73/64.56 |
| 8,865,458 B2* | 10/2014 | Ramsey | ............... | A61B 10/007 422/401 |
| 9,011,770 B2* | 4/2015 | Wu | ................... | B01L 3/502 422/63 |
| 9,291,515 B2* | 3/2016 | Ling | ................... | G01L 7/18 |
| 2003/0022392 A1* | 1/2003 | Hudak | ................... | B01L 3/502 436/518 |
| 2003/0027359 A1* | 2/2003 | Hudak | ................... | B01L 3/502 436/518 |
| 2004/0136877 A1* | 7/2004 | Kang | ................ | A61B 10/0096 422/417 |
| 2007/0275475 A1* | 11/2007 | Liang | ................... | B01L 3/502 436/165 |
| 2010/0266449 A1* | 10/2010 | Wu | ................... | A61B 10/0045 422/423 |
| 2011/0107824 A1* | 5/2011 | Lv | ................... | A61B 10/0045 73/64.56 |
| 2013/0291659 A1* | 11/2013 | Ling | ................... | G01L 7/18 73/863.02 |

* cited by examiner

BODY FLUID TESTING APPARATUS

CROSS-REFERENCE TO RELATED DISCLOSURES

This application claims the benefit of Chinese Patent Application No. 201210229325.8, filed on Jul. 3, 2012 and entitled "BODY FLUID TESTING APPARATUS", the content of which is incorporated by reference herein in its entirety.

TECHNICAL FIELD

The present disclosure relates to an apparatus for testing fluid, and particularly to a body fluid testing apparatus, which belongs to the field of medical apparatus.

BACKGROUND ART

Many metabolites in the body can be detected by testing body fluids, such as urine, which has become an important test in the physical examination. For example, the particular drugs taken by the drug addicts usually can be detected in their urine. Thus, urine collection containers for testing drugs are required by many medical institutions and police stations.

U.S. Pat. No. 6,576,193 discloses a urine collection container that comprises: a first compartment for receiving a fluid specimen to be tested; a rotatable valve having one or more wells formed on its surface; and a second compartment. Said wells are in fluid connection with the first compartment when the valve is at a first valve position and in fluid connection with the second compartment when the valve is at a second valve position. In order to achieve the technical solution thereof, this device should provide multiple wells formed on the surface of the valve.

U.S. Pat. App. No. 20030027359 discloses a specimen collection device that includes a reservoir chamber; a testing chamber; and a plunger chamber for separating the reservoir chamber and testing chamber. The valve plunger is capable of transferring at least a portion of the specimen from the reservoir chamber to the testing reservoir, and the reservoir chamber and the testing reservoir are not in direct fluid communication. When the valve plunger is at a first position, the plunger chamber is fluidly connected to the reservoir chamber and not connected to the testing chamber. When the valve plunger is at a second position, the plunger chamber is neither fluidly connected to the reservoir chamber nor to the testing chamber. In order to achieve the technical solution thereof, this device should provide a chamber capable of collecting fluid specimens inside the plunger.

CN Pat. No. 200820001694.0 discloses a device for collecting and testing fluid specimens that includes a collecting cup; a testing means with testing cards; a specimen holder with the collecting cup and the testing mean fixed thereon; and a cup cover. A collecting chamber is located at the lower part of the collecting cup, which has an opening on one end and has a collecting plug disposed therein with unitary structure. The collecting plug has at least one ring groove and at least one sealing ring. In order to achieve the technical solution thereof, this device also should provide a reservoir chamber inside the plunger.

SUMMARY OF THE DISCLOSURE

An object of the present disclosure is to provide a body fluid testing apparatus.

In one aspect, a body fluid testing apparatus, comprising a containing chamber having a first opening on the bottom wall thereof; a plunger chamber having a second opening on the bottom wall thereof, wherein the plunger chamber is disposed below the bottom wall of the containing chamber and in communication with the containing chamber through the first opening; a plunger received in the plunger chamber and contacting with the side wall of the plunger chamber; a testing chamber positioned exterior to the side wall of the containing chamber and in communication with the plunger chamber through the second opening; and a testing card received in the testing chamber and designed to contain test strips; wherein, the axial of the plunger is perpendicular to the testing card.

According to some embodiments, the body fluid is urine.

According to some embodiments, the area ratio of the first opening to the bottom wall of the containing chamber is in a range from $1/200$ to $1/25$.

According to some embodiments, the plunger chamber comprises a first chamber, a second chamber and a third chamber sequentially away from the testing chamber.

According to some embodiments, each of the first chamber and the second chamber has a cylindrical shape, and the third chamber is cone frustum shaped.

According to some embodiments, the first chamber and the second chamber have a diameter equal to that of the plunger, and the third chamber has a minimum diameter equal to than that of the plunger.

According to some embodiments, the plunger further comprises at least one sealing ring on the periphery thereof.

According to some embodiments, the diameter of the second opening is $1/30$ to $1/10$ of the diameter of the bottom wall of the plunger chamber, and the distance from the center of the second opening to the end of the bottom wall of the containing chamber facing the plunger chamber is $1/4$ to $3/4$ of the diameter of the bottom wall of the plunger chamber.

According to some embodiments, the second opening is sealed by a waterproof label.

According to some embodiments, the second opening is sealed by a sealing pipe, and a first plug is disposed on one end of the sealing pipe and in communication with the sealing pipe, and has an outer diameter equal to the diameter of the second opening.

According to some embodiments, the sealing pipe extends from the bottom wall of the plunger chamber to the back of the testing card in the testing chamber, then runs along the back of testing card from bottom to top and reaches a top edge of the testing card, and finally extends downward along a top part of the card slot.

According to some embodiments, the apparatus further comprises a buffer chamber which is disposed below the bottom wall of the containing chamber and between the plunger chamber and the testing chamber.

According to some embodiments, the buffer chamber comprises an end surface, which is disposed between the testing chamber and the buffer chamber and extends downwards from the side wall of the containing chamber, and wherein a gap exists in one end of the end surface away from the containing chamber and allows the body fluid run through.

According to some embodiments, the bottom of the buffer chamber opposite to the bottom wall of the containing chamber takes a form of a slope.

According to some embodiments, the apparatus further comprises a cup body and a cup holder which is coupled with the inner bottom of the cup body.

According to some embodiments, one side of the cup holder facing the cup body serves as one part of the buffer chamber, and the lower part of the cup body serves as another part of the buffer chamber, and when the cup holder is coupled with the cup body, the buffer chamber is formed.

According to some embodiments, a card slot is formed on the side of the cup holder facing the cup body, and a card cover corresponding to the card slot is also formed on the cup body, and when the cup holder is coupled with the cup body, a card chamber is formed.

DETAILED DESCRIPTION

Embodiment 1

Figure 1:
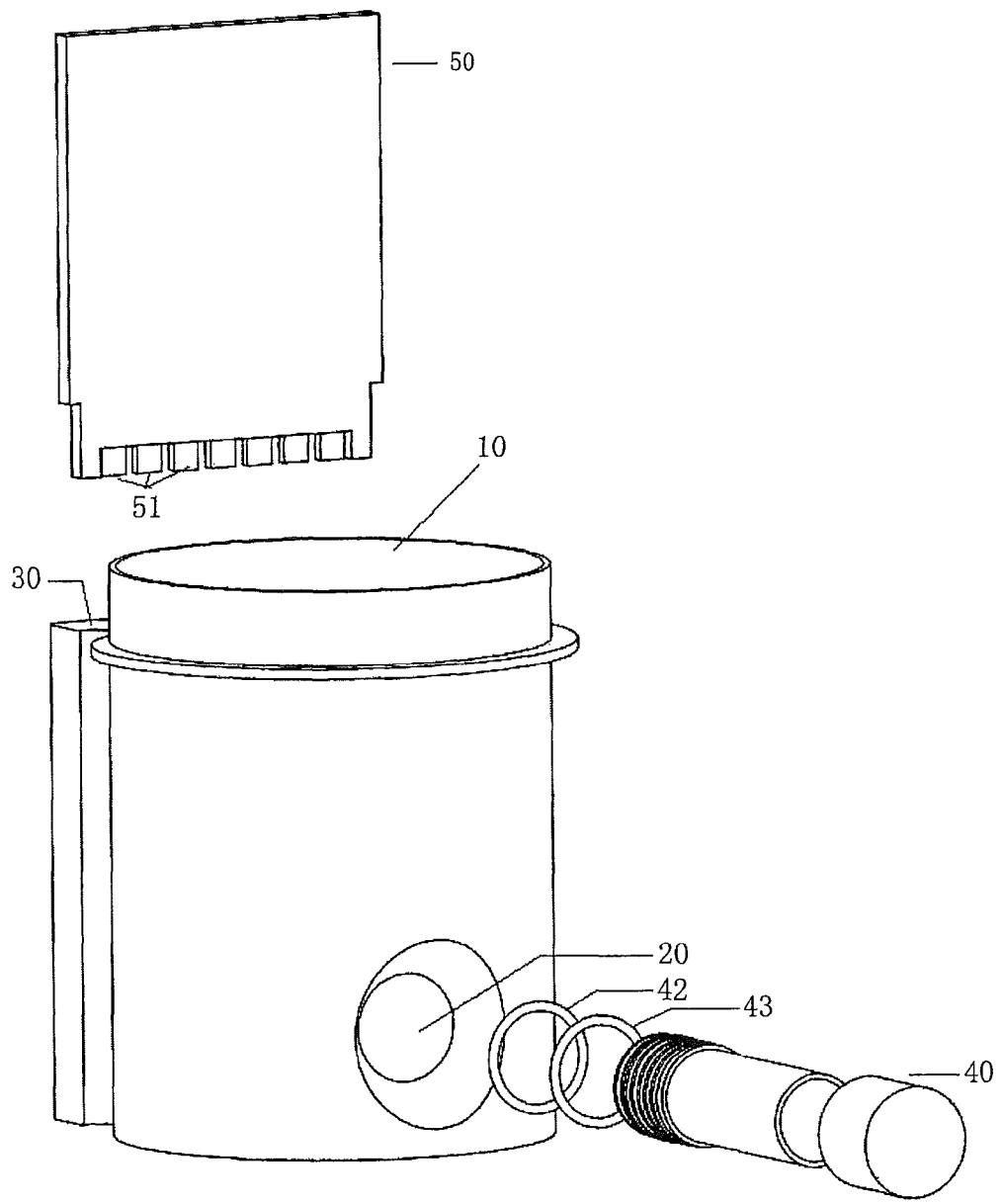
FIG. 1 illustrates an exploded view of the body fluid testing apparatus according to Embodiment 1 of the present disclosure.
Figure 2:
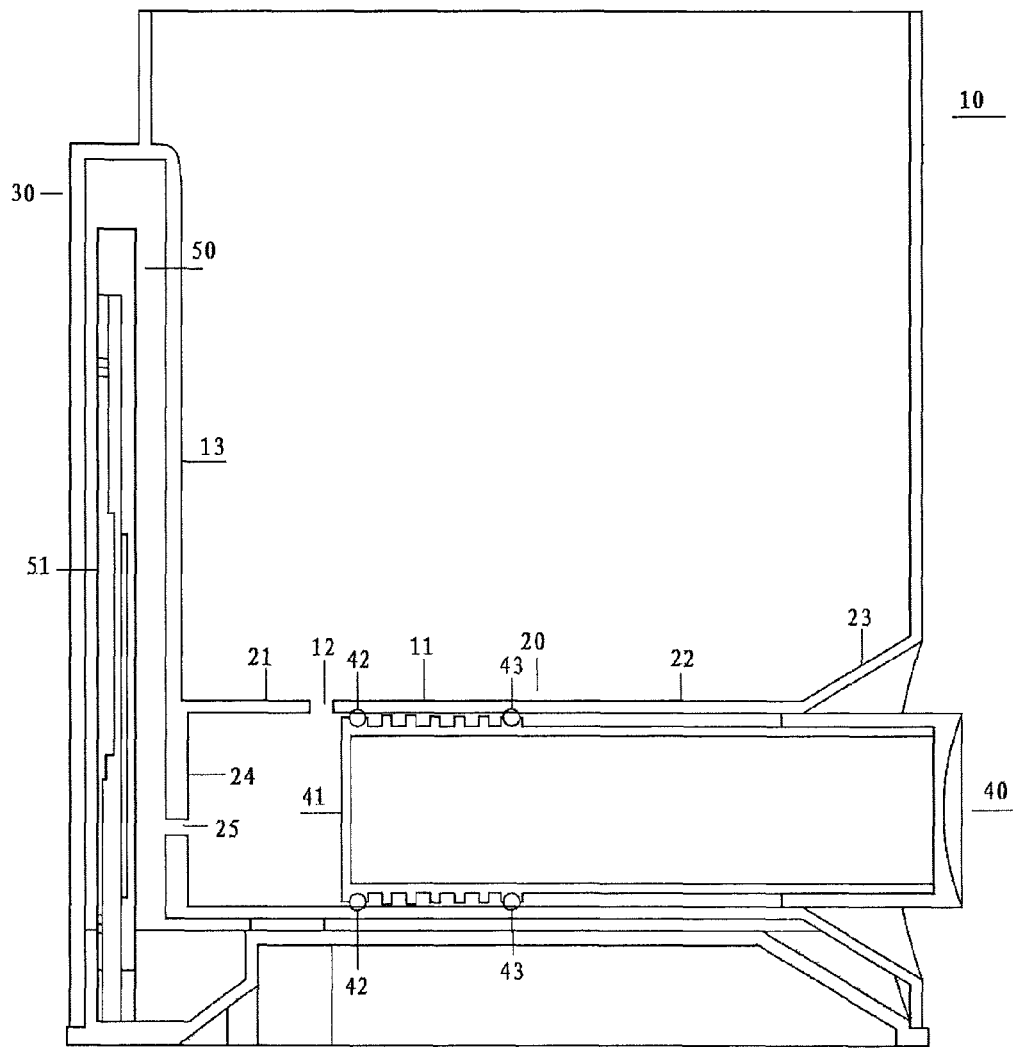
FIG. 2 illustrates a sectional view of the body fluid testing apparatus according to Embodiment 1 of the present disclosure when the plunger is at a first position.

Referring to FIGS. 1-2, the body fluid testing apparatus comprises a containing chamber 10, a plunger chamber 20, a testing chamber 30, a plunger 40 and a testing card 50. The plunger chamber 20 is positioned below the bottom wall 11 of the containing chamber 10, and the testing chamber 30 is positioned exterior to the side wall 13 of the containing chamber 10. The plunger 40 is disposed in the plunger chamber 20 and is provided with one or more sealing rings on its periphery, for example sealing rings 42 and 43. The testing card 50 is received in the testing chamber 30, and a variety of testing strips 51 are contained in the testing card 50, each of which is used for testing one or more drugs, alcohol or other illicit drugs taken by the subjects.

The plunger chamber 20 comprises a first chamber 21, a second chamber 22 and a third chamber 23. The first chamber 21 is formed between the bottom 41 of the plunger facing the testing chamber and the plunger chamber 20, when the plunger is at the first position as shown in FIG. 2, that is to say, when the plunger is located in the second chamber and the third chamber, but not pushed into the first chamber. Referring to FIG. 2 in combination with FIG. 1, it can be seen that each of the first chamber 21 and the second chamber 22 has a cylindrical shape with the same diameter, and the third chamber 23 is cone frustum shaped and has a minimum diameter equal to that of the first chamber and the second chamber. The third chamber 23 with cone frustum shape facilitates the operator to push the plunger due to the larger end of the third chamber.

The containing chamber 10 comprises a bottom wall 11 with a first opening 12, through which the containing chamber 10 is communicated with the plunger chamber 20. The diameter ratio of the first opening 12 to the bottom wall 11 is about ⅓. A second opening 25 is provided in the bottom wall 24 of the plunger chamber 20. The diameter ratio of the second opening 25 to the bottom wall 24 is about ⅛. The distance from the center of the second opening 25 to the side of the bottom wall of containing chamber facing the plunger chamber is ½ of the length of the bottom wall of the plunger chamber. The testing chamber 30 is communicated with the plunger chamber 20 through the second opening 25.

The plunger 40 is capable of being received in the plunger chamber 20 and contacted with the side wall 44 of the plunger chamber 20. The axial of the plunger 40 is perpendicular to the testing card 50. The plunger 40 is provided with the sealing rings 42 and 43 on its periphery to prevent the body fluid in the first chamber 21 from leaking from the plunger chamber.

The testing card 50 with test strips 51 is disposed in the testing chamber 30. The testing chamber 30 is formed outwardly from the side wall 13 of the containing chamber 10 and extends from the bottom of the apparatus to a position near the top of the containing chamber 10. The shape of the testing chamber 30 is similar to that of the testing card 50, and in this embodiment, the testing chamber 30 is rectangular in shape. The volume of the testing chamber 30 is larger than that of the testing card 50.

As can be seen from FIG. 1, when the plunger 40 is at the first position, the body fluid runs from the containing chamber 10 into the first chamber 21 through the first opening 12. Due to the effect of the surface tension, the body fluid in the first chamber can not enter the testing chamber 30.

Figure 3:
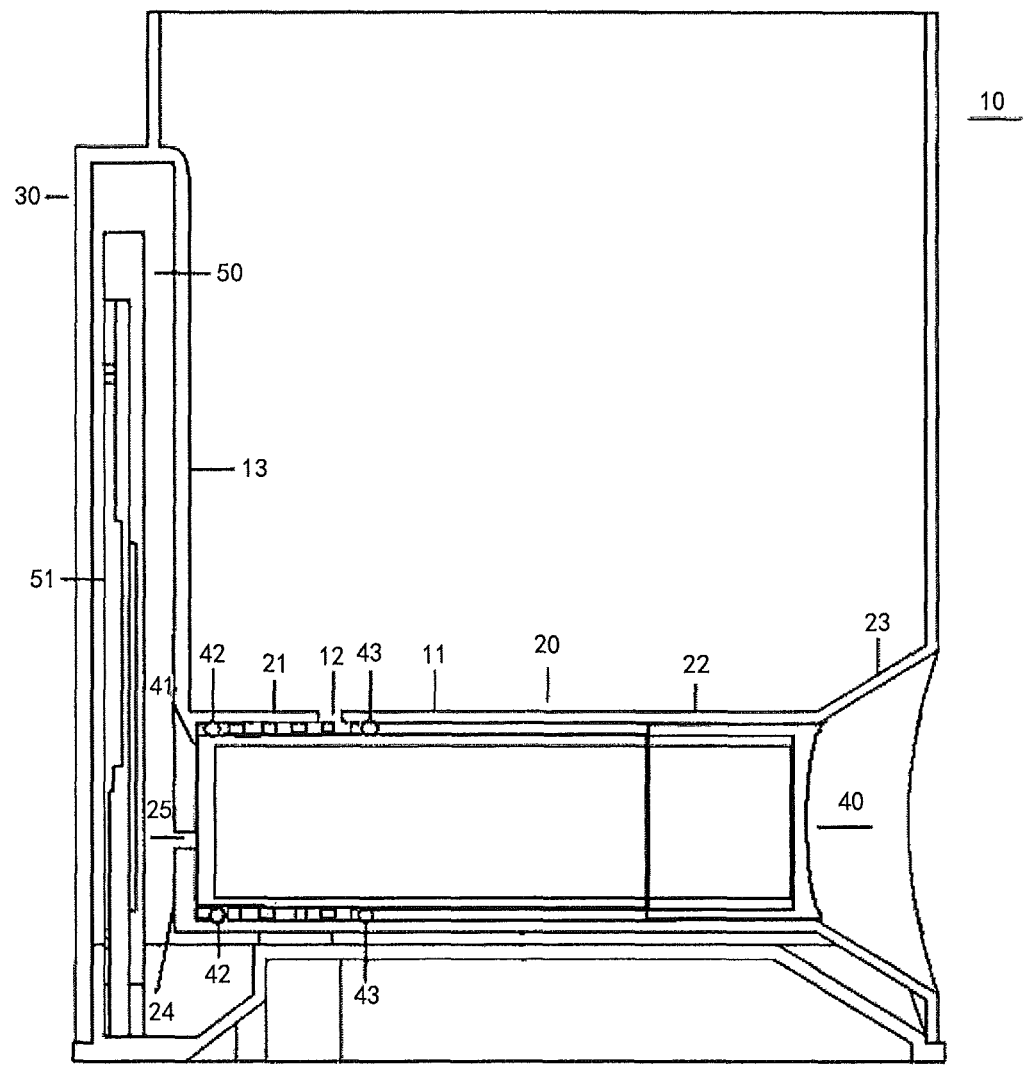
FIG. 3 illustrates a sectional view of the body fluid testing apparatus according to Embodiment 1 of the present disclosure when the plunger is at a second position.

Referring to FIG. 3, when the plunger 40 moves towards the testing chamber 30, the body fluid in the first chamber 21 runs into the testing chamber 30 through the second opening 25.

When in use, the plunger 40 is initially disposed at the first position as shown in FIG. 2. Meanwhile, the subject's urine in the containing chamber 10 runs into the first chamber 21 of the plunger chamber 20 through the first opening 12 in the bottom wall 11 of the containing chamber 10. Urine in the first chamber 21 can not enter the testing chamber 30 by itself, because the second opening 25 on the bottom wall 24 of the plunger chamber 20 is very small. When the plunger 40 is pushed towards the testing chamber 30, urine can enter into the testing chamber 30 through the second opening 25 in the bottom wall 24 of the plunger chamber 20. Once urine is contacted with the bottom of the test strip in the testing card 50, color will appear on the test strip. The color can demonstrate whether the subject has taken the drug, alcohol or other illicit drugs or not, and the particular type of the drug or other illicit drugs also can be determined according to the color.

Embodiment 2

Figure 4:
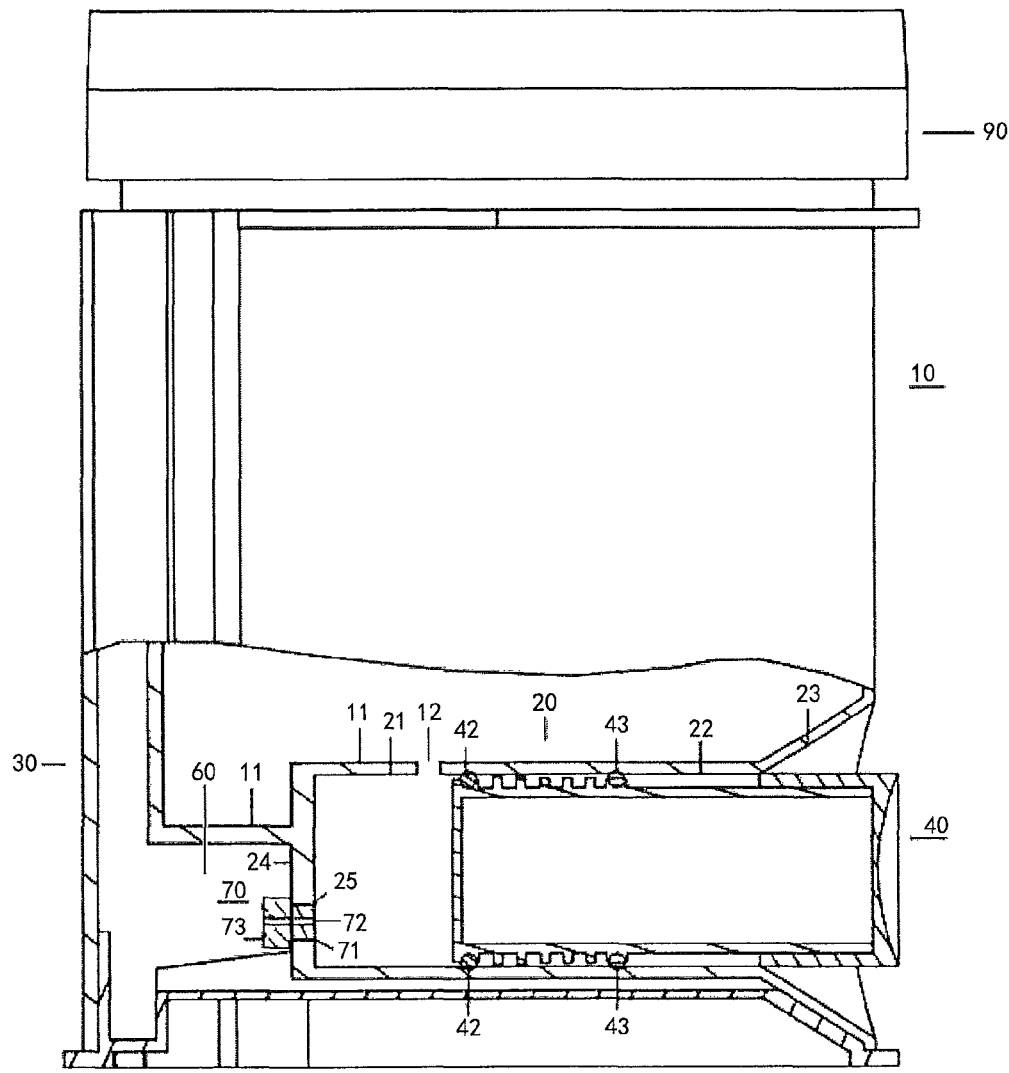
FIG. 4 illustrates a sectional view of the body fluid testing apparatus according to Embodiment 2 of the present disclosure when the plunger is at a first position.
Figure 6:
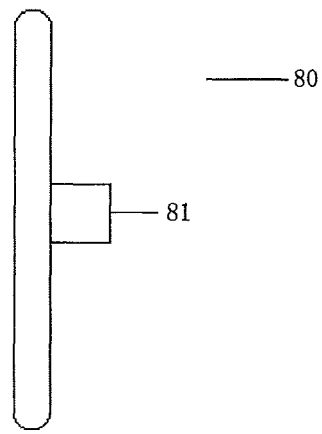
FIG. 6 illustrates a side view of a waterproof label.

Referring to FIG. 4, in this embodiment, a buffer chamber 60 is further disposed between the plunger chamber 20 and the test chamber 30 below the bottom wall 11 of the containing chamber 10. A second opening 25 is arranged on the common bottom wall 24 of the buffer chamber 60 and the plunger chamber 20, and sealed by a sealing pipe 70 or a waterproof label 80 as shown in FIG. 6. In this embodiment, the apparatus further comprises a cover 90 coupled with the containing chamber 10.

Figure 5:
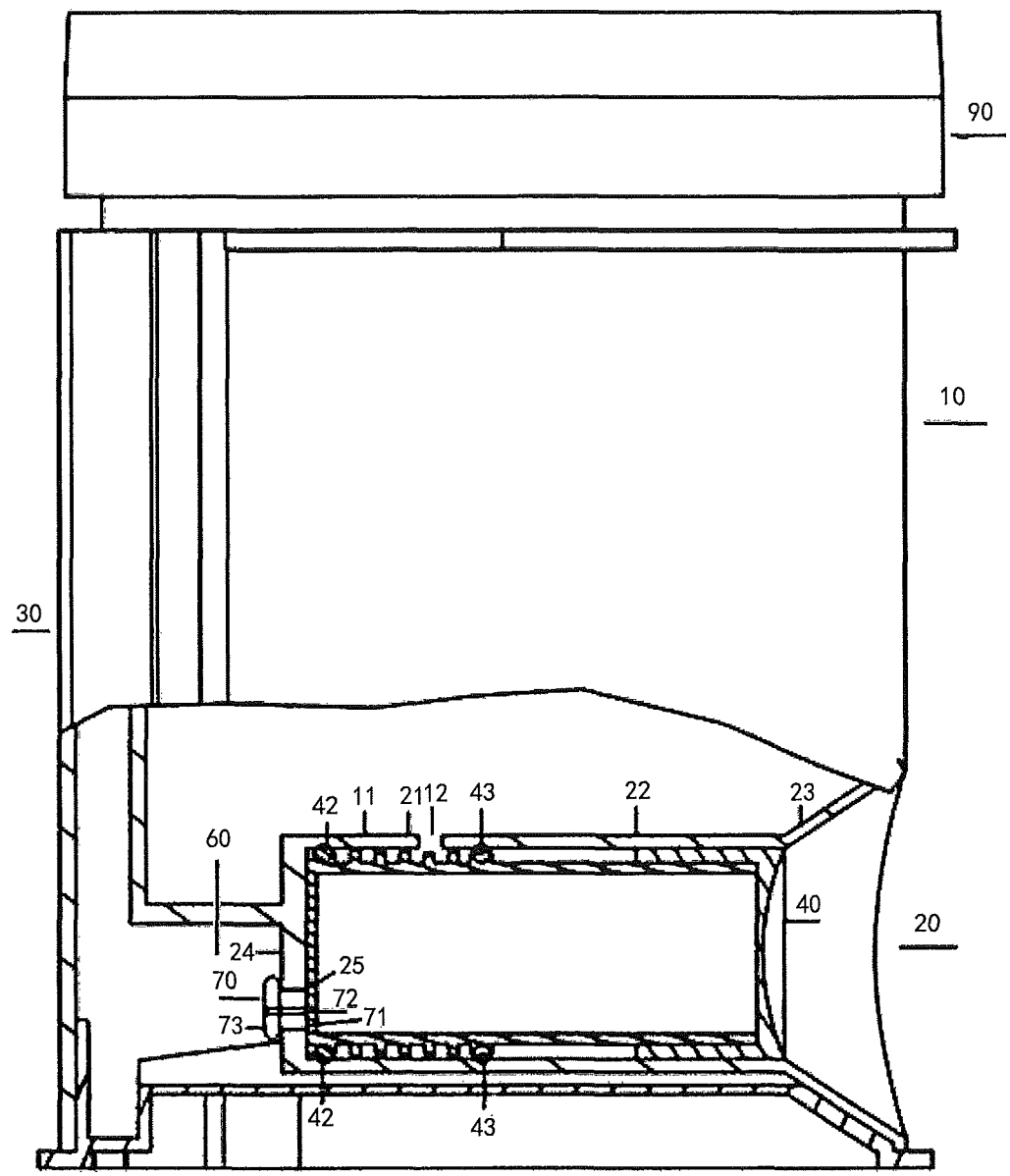
FIG. 5 illustrates a sectional view of the body fluid testing apparatus according to Embodiment 2 of the present disclosure when the plunger is at a second position.

When the second opening 25 of the plunger chamber 20 is sealed by the waterproof label, the diameter ratio of the second opening 25 to the bottom wall 24 of the plunger chamber 20 is 1/15, and the distance from the center of the second opening 25 to the side of the bottom wall of the containing chamber facing the plunger chamber is 1/4 of the length of the bottom wall of the plunger chamber. When the plunger 40 is at the first position, urine runs from the containing chamber 10 into the first chamber 21 through the first opening 12. When the plunger moves from the first position to the second position as shown in FIG. 5, the urine bursts open the waterproof label 80 at the bottom wall 24 of the plunger chamber and enters into the buffer chamber 60, and then reaches the test chamber 30 through the buffer chamber 60.

When the second opening 25 of the plunger chamber 20 is sealed by the sealing pipe 70, urine runs from the containing chamber 10 into the first chamber 21 through the first opening 12 as the plunger 40 is at the first position. When the plunger 40 moves from the first position to the second position as shown in FIG. 5, urine enters the buffer chamber 60 via the through-hole 72 of the sealing pipe 70 as shown in FIG. 7 and finally reaches the test chamber 30 through the buffer chamber 60 to perform the test.

Referring to FIG. 6, the waterproof label 80 may comprises a second plug 81, which is coupled with the second opening 25 at the bottom wall 24 of the plunger chamber 20. Alternatively, the waterproof label 80 may not comprise the second plug 81.

Figure 7:
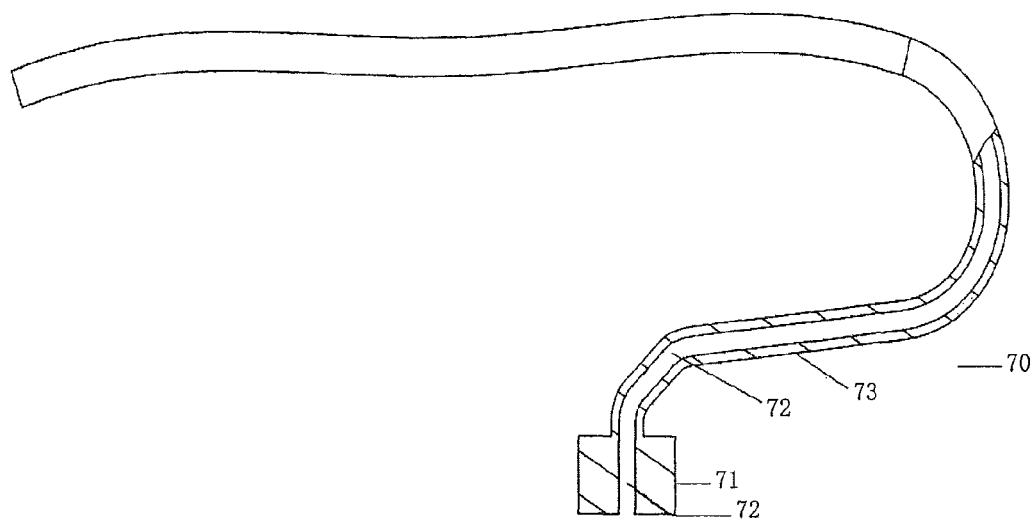
FIG. 7 illustrates a sectional view of a sealing pipe.

Referring to FIG. 7, the sealing pipe 70 comprises a first plug 71. The through-hole 72 of the sealing pipe 70 fully runs through both the plug 71 and the whole pipe 73.

When the second opening 25 at the bottom wall 24 of the plunger chamber 20 is sealed by the sealing pipe 70, the plunger 40 is initially disposed at the first position as shown in FIG. 4. The subject's urine contained in the containing chamber 10 enters the first chamber 21 of the plunger chamber 20 through the first opening 12 on the bottom wall 11 of the containing chamber 10. Urine in the first chamber 21 can not run into the test chamber 30 by itself, because the second opening 25 on the bottom wall 24 of the first chamber 21 is plugged by the sealing pipe 70. When the plunger 40 is pushed towards the testing chamber 30 and reaches the second position as shown in FIG. 5, urine runs into the buffer chamber 60 and the test chamber 30 via the through-hole 72 of the sealing pipe 70 in turn. Once urine in the test chamber 30 contacts with the bottom of the test strip 51 in the testing card 50, color will appear on the test strip. The color can demonstrate whether the subject has taken the drug, alcohol or other illicit drugs or not, and the particular type of the drug or other illicit drugs can be determined according to the color.

When the second opening 25 on the bottom wall 24 of the plunger chamber 20 is sealed by the waterproof label 80, the subject's urine in the containing chamber 10 runs from the containing chamber 10 into the first chamber 21 through the first opening 12, as the plunger 40 is at the first position. Urine can not run from the plunger chamber 20 into the buffer chamber 60, because the second opening 25 on the bottom wall 24 of the plunger chamber 20 is sealed by the second plug 81 of the waterproof label 80. The second opening 25 on the bottom wall 24 of the plunger chamber can also be directly sealed by a waterproof 80 without the second plug 81. When the plunger moves from the first position to the second position, urine bursts open the waterproof label 80 on the bottom wall 24 of the plunger chamber 20 and enters into the buffer chamber 60, and then reaches the test chamber 30 through the buffer chamber 60. Once urine contacts with the bottom of the test strip in the testing card 50, color will appear on the test strip. The color can demonstrate whether the subject has taken the drug, alcohol or other illicit drugs or not, and the particular type of the drug or other illicit drugs can be determined according to the color.

Embodiment 3

Figure 8:
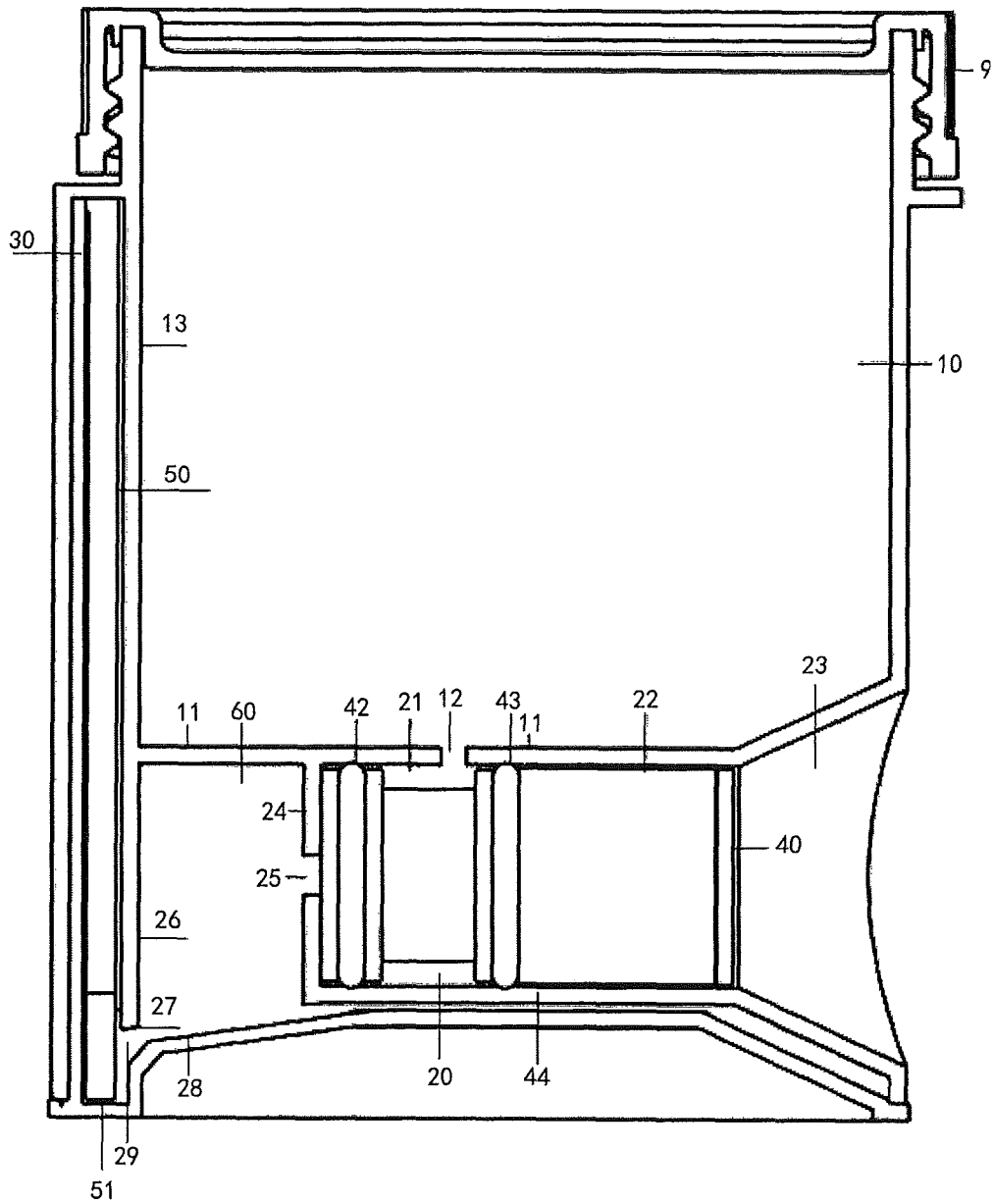
FIG. 8 illustrates a sectional view of the body fluid testing apparatus according to Embodiment 3 of the present disclosure.

Referring to FIG. 8, this embodiment is substantially the same as the embodiment 2, except that the buffer chamber 60 according to this embodiment comprises an end surface 26 between the test chamber 30 and the buffer chamber 60, which extends downwards from the side wall 13 of the containing chamber 10. A gap 29 exists between one end of the end surface 26 away from the containing chamber 10 and the bottom wall 28 of the buffer chamber 60 to allow the body fluid run through. The bottom wall 28 of the buffer chamber 60 opposes to the bottom wall 11 of the containing chamber 10. In this embodiment, the bottom wall 28 of the buffer chamber 60 takes the form of a slope. When the body fluid is pushed from the plunger chamber 20 into the buffer chamber 60 by the plunger 40, it tends to splash on the back of the testing card 50 or heavy impacts the test strip 51, such that the test may fail due to the damage of the test strip. As a result of the design of a slope according to this embodiment, the body fluid will firstly splash on the end surface 26, then pass through the gap 29 along the end surface 26 and the bottom wall 28 of the buffer chamber 60, and subsequently contact with the test strip 51, when pushed from the plunger chamber 20 into the buffer chamber 60 by the plunger 40. Therefore, the damage of the test strip can be effectively avoided, allowing a high success rate for the test.

Embodiment 4

Figure 9:
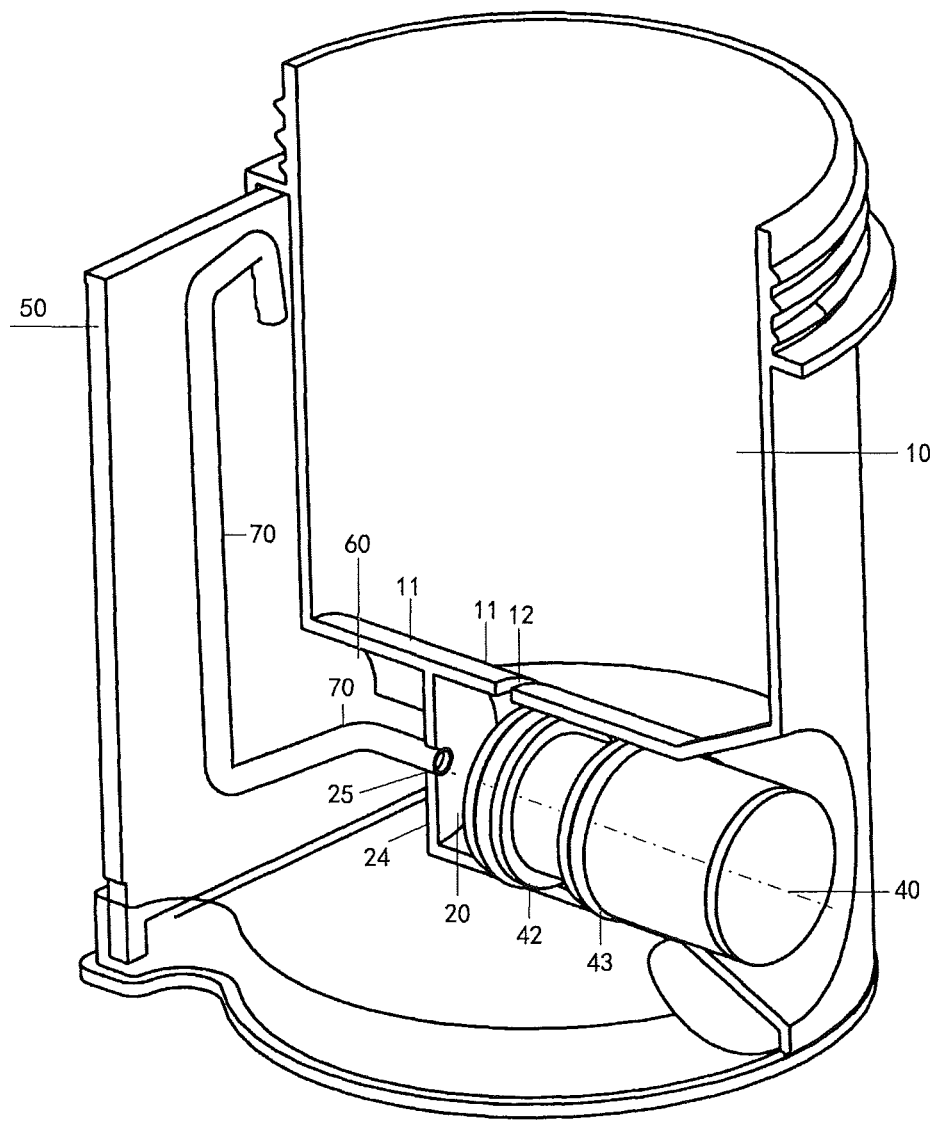
FIG. 9 illustrates a partial sectional view of the body fluid testing apparatus according to Embodiment 4 of the present disclosure.

Referring to FIG. 9, this embodiment is substantially the same as the embodiment 2, except that the sealing pipe 70 is U-shaped. One end of the sealing pipe 70 seals second opening 25 of the plunger chamber 20, meanwhile, the other end of the sealing pipe 70 extends from the bottom wall 24 of the plunger chamber 20 to the back of the testing card 50 in the test chamber 30, and then extends from bottom to top along the back of the testing card 50 to the top of the testing card 50, and finally extends downwards from the top of the testing card 50. Due to the design of the U-shaped sealing pipe, the possibility of the damage of the test strip can be effectively decreased, when the body fluid to be tested is released from top to bottom along the sealing pipe 70.

Embodiment 5

Figure 10:
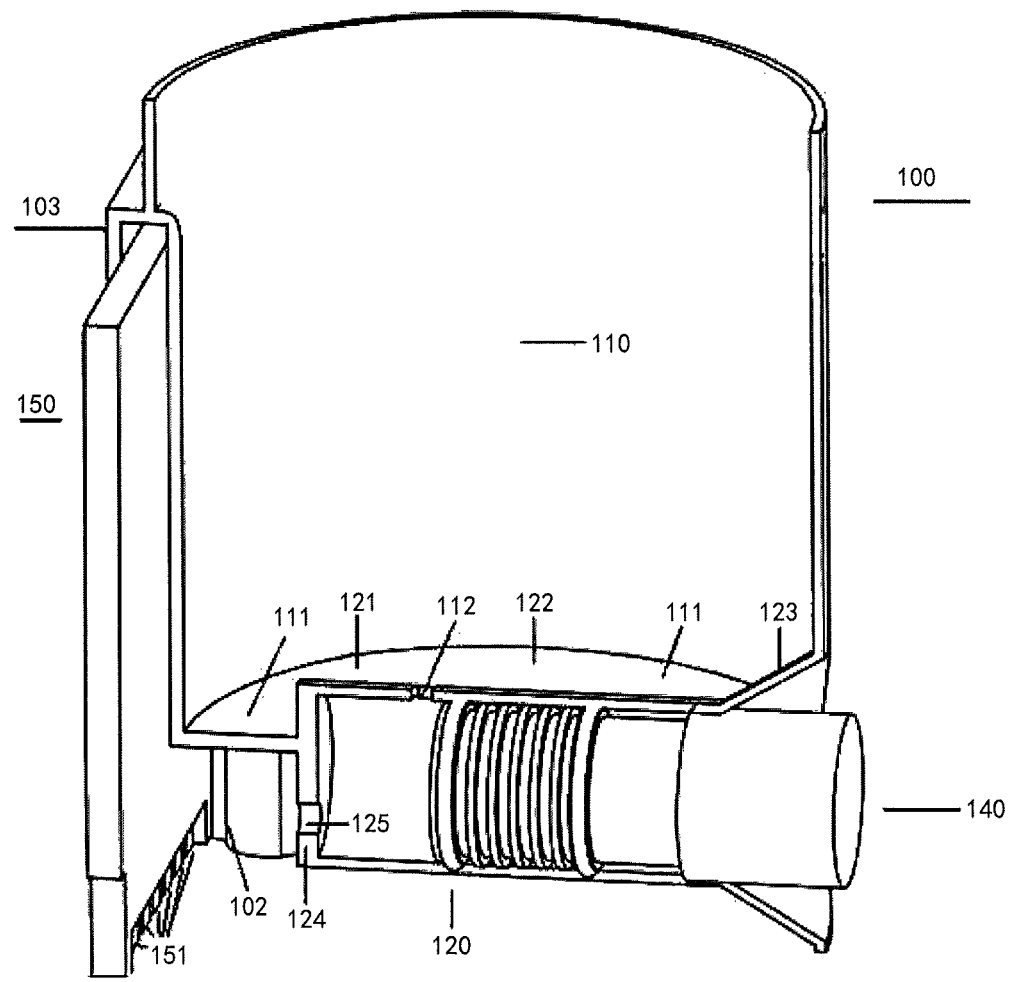
FIG. 10 illustrates a partial sectional view of the cup body of the body fluid testing apparatus according to Embodiment 5 of the present disclosure.
Figure 11:
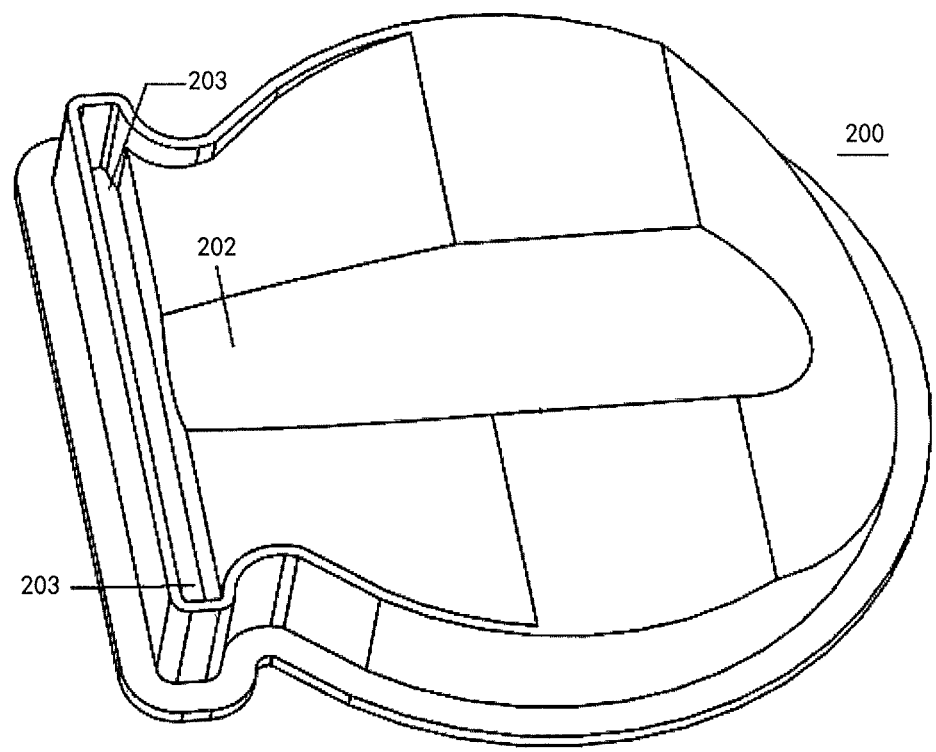
FIG. 11 illustrates a perspective view of the cup holder of the body fluid testing apparatus according to Embodiment 5 of the present disclosure.

Referring to FIG. 10, the body fluid testing apparatus comprises a cup body 100 and a cup holder 200 as shown in FIG. 11. The bottom of the cup body 100 forms the plunger chamber 120, one part of the buffer chamber 102 and the card cover 103. The inner bottom of the cup body is coupled with the cup holder 200 as shown in FIG. 11.

The cup body 100 comprises a containing chamber 110. A first opening 112 is provided on the bottom wall 111, through which the containing chamber 110 is communicated with the plunger chamber 120. The cup body further comprises a bottom wall 124 between the plunger chamber 120 and the part of the buffer chamber 102. A second opening 125 is provided on the bottom wall 124, through which the plunger chamber 120 is in communicated with the part of the buffer chamber 102. The second opening 125 is sealed by the waterproof label as shown in FIG. 6 or by the sealing pipe as shown in FIG. 7. For the description of the sealing pipe and the waterproof label, one may see the embodiment 2.

The plunger chamber 120 with a plunger 140 disposed therein comprises a first chamber 121, a second chamber 122 and a third chamber 123.

A testing card 150 with test strip 151 is disposed in the card cover 103.

Referring to FIG. 11, one side of the cup holder 200 facing the cup body forms the other part of the buffer chamber 202 and a card slot 203. The card slot 203 is perpendicular to the axial of the other part of the buffer chamber 202. The card cover 103 and the card slot 203 of the cup holder are combined to form the card chamber. The part of the buffer chamber 102 on the inner bottom of the cup body and the other part of the buffer chamber 202 of the cup holder are combined to form the buffer chamber.

The usage thereof is similar to that of the embodiment 2.

The present disclosure may have at least one of the technical effects as described below:

1. The apparatus according to the present disclosure features a simple structure and a convenient operation.

2. The apparatus according to the present disclosure can carry out the test of the body fluid, even though a chamber for the plunger in the prior art is omitted.

3. The axial of the plunger chamber and/or the buffer chamber of the apparatus according to the present disclosure is perpendicular to the test chamber, which makes the structure of the apparatus more novel and fashion.

Exemplary embodiments have been specifically shown and described as above. It will be appreciated by those skilled in the art that the disclosure is not limited to the disclosed embodiments; rather, all suitable modifications and equivalent which come within the spirit and scope of the appended claims are intended to fall within the scope of the disclosure.

What is claimed is:

1. A body fluid testing apparatus, comprising a containing chamber having a first opening on a bottom wall thereof; a plunger chamber having a second opening on a bottom wall thereof protruding from the bottom wall of the containing chamber, wherein the plunger chamber is disposed below the bottom wall of the containing chamber and in communication with the containing chamber through the first opening; a plunger received in the plunger chamber, having a cylinder-like shape and contacting with a side wall of the plunger chamber which is substantially perpendicular to the bottom wall of the plunger chamber and opposite to the bottom wall of the containing chamber with reference to the plunger; a testing chamber positioned exterior to the side wall of the containing chamber and in communication with the plunger chamber through the second opening; and a testing card received in the testing chamber, having a plane shape and designed to contain test strips; wherein, an axis of the plunger is perpendicular to the testing card.

2. The apparatus according to claim 1, wherein the body fluid is urine.

3. The apparatus according to claim 1, wherein an area ratio of the first opening to the bottom wall of the containing chamber is in a range from 1/200 to 1/25.

4. The apparatus according to claim 1, wherein the plunger further comprises at least one sealing ring on a periphery thereof.

5. The apparatus according to claim 1, wherein a diameter of the second opening is 1/30 to 1/10 of a diameter of the bottom wall of the plunger chamber, and the distance from a center of the second opening to a side of the bottom wall of the containing chamber facing the plunger chamber is 1/4 to 3/4 of the diameter of the bottom wall of the plunger chamber.

6. The apparatus according to claim 1, wherein the second opening is sealed by a waterproof label.

7. The apparatus according to claim 1, wherein the second opening is sealed by a sealing pipe, and a first plug is disposed on one end of the sealing pipe and in communication with the sealing pipe, and has an outer diameter equal to a diameter of the second opening.

8. The apparatus according to claim 7, wherein the sealing pipe extends from the bottom wall of the plunger chamber to a back of the testing card in the testing chamber, then runs along the back of testing card from bottom to top and reaches a top edge of the testing card, and finally extends downward along a top part of the testing card.

9. The apparatus according to claim 1, wherein the plunger chamber comprises a first chamber, a second chamber and a third chamber sequentially away from the testing chamber.

10. The apparatus according to claim 9, wherein each of the first chamber and the second chamber has a cylindrical shape, and the third chamber is cone frustum shaped.

11. The apparatus according to claim 10, wherein the first chamber and the second chamber have a diameter equal to that of the plunger, and the third chamber has a minimum diameter equal to that of the plunger.

12. The apparatus according to claim 1, wherein the apparatus further comprises a buffer chamber which is disposed below the bottom wall of the containing chamber and between the plunger chamber and the testing chamber.

13. The apparatus according to claim 12, wherein the buffer chamber comprises an end surface, which is disposed between the testing chamber and the buffer chamber and extends downwards from the side wall of the containing chamber, and wherein a gap exists in one end of the end surface away from the containing chamber and allows the body fluid run through.

14. The apparatus according to claim 12, wherein the bottom of the buffer chamber opposite to the bottom wall of the containing chamber takes a form of a slope.

15. The apparatus according to claim 1, wherein the apparatus further comprises a cup body and a cup holder which is coupled with the inner bottom of the cup body.

16. The apparatus according to claim 15, wherein one side of the cup holder facing the cup body serves as one part of a buffer chamber, and a lower part of the cup body serves as another part of the buffer chamber, and when the cup holder is coupled with the cup body, the buffer chamber is formed.

17. The apparatus according to claim 15, wherein a card slot is formed on a side of the cup holder facing the cup body, and a card cover corresponding to the card slot is also formed on the cup body, and when the cup holder is coupled with the cup body, a card chamber is formed.

* * * * *